United States Patent [19]

Huene

[11] Patent Number: 4,963,144
[45] Date of Patent: Oct. 16, 1990

[54] BONE SCREW FIXATION ASSEMBLY, BONE SCREW THEREFOR AND METHOD OF FIXATION

[76] Inventor: Donald R. Huene, 201 N. Valeria, Fresno, Calif. 93701

[21] Appl. No.: 324,702

[22] Filed: Mar. 17, 1989

[51] Int. Cl.$^5$ .............................................. A61B 17/58
[52] U.S. Cl. ....................................... 606/73; 606/72; 606/104
[58] Field of Search ................. 128/92 R, 92 E, 92 V, 128/92 VT, 92 Z, 92 ZZ, 92 YV, 92 VW, 92 YF; 81/459; 606/72, 73, 104; 623/18

[56] References Cited

U.S. PATENT DOCUMENTS

| 1,007,107 | 10/1911 | Hulsmann | 81/459 |
|---|---|---|---|
| 2,121,193 | 6/1938 | Hanicke | 128/92 VT |
| 2,312,869 | 3/1943 | Boyer | 128/92 V |
| 2,329,398 | 9/1943 | Duffy | 128/92 V |
| 3,604,487 | 9/1971 | Gilbert | 145/50 D |
| 3,867,932 | 2/1975 | Huene | 128/92 E |
| 4,793,335 | 12/1988 | Frey et al. | 606/73 |

FOREIGN PATENT DOCUMENTS

| 317406 | 5/1989 | European Pat. Off. | 606/73 |
|---|---|---|---|
| 2933141 | 4/1980 | Fed. Rep. of Germany | 623/18 |
| 3119583 | of 1982 | Fed. Rep. of Germany | 128/92 V |
| 575090 | of 1977 | U.S.S.R. | 128/92 VT |
| 0575090 | 10/1977 | U.S.S.R. | 128/92 VT |
| 940375 | of 1980 | U.S.S.R. | 128/92 V |
| 0827050 | 5/1981 | U.S.S.R. | 128/92 YF |
| 940376 | of 1985 | U.S.S.R. | 128/92 V |

OTHER PUBLICATIONS

John B. McGinty, Techniques in Orthepaedics, vol. 5, Arthrosopic Surgery Update, 1985, pp. 73-77.
T. David Sisk, Campbell's Operative Orthopedics, vol. 4, 7th Edition, Arthroscopy of Knee and Ankle, Chapter 59, pp. 2547, 2597-2598, 1987.
C. McCollister Evarts, Surgery of the Musculoskeltal System, 1983, The Knee, pp. 7:348-350.
Larry L. Johnson, Arthroscopic Surgery Principles and Practice, 1986, pp. 685-696.

Primary Examiner—Robert A. Hafer
Assistant Examiner—Kevin G. Kooney
Attorney, Agent, or Firm—Shlesinger & Myers

[57] ABSTRACT

A bone screw fixation assembly comprises a longitudinally extending member having an aperture therethrough defining an inner wall with spaced first and second end portions. A first set of threads are formed in the inner wall at the first end portion for receiving a cooperating second set of threads disposed about the exterior of a fixation device. A longitudinally extending fam rod has first and second spaced ends, and the jam rod is receivable in the aperture for permitting the jam rod first end to engage the fixation device when received within the member first end portion. A locking mechanism is operably associated with the member for selectively locking the jam rod in engagement with the received fixation device so that movement of the first set of threads relative to the second set of threads is prevented.

22 Claims, 3 Drawing Sheets

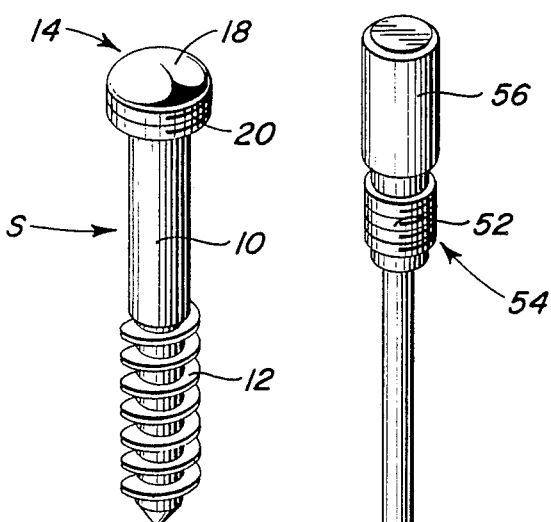
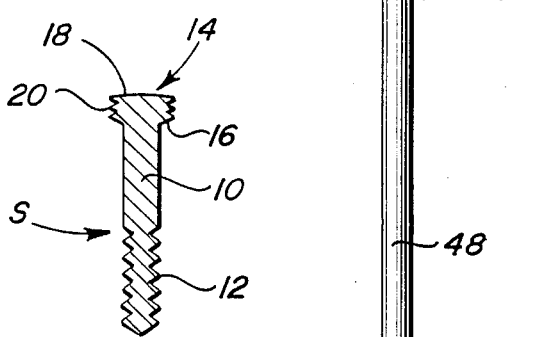
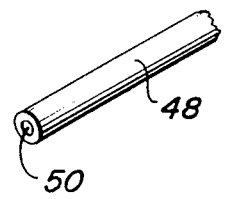
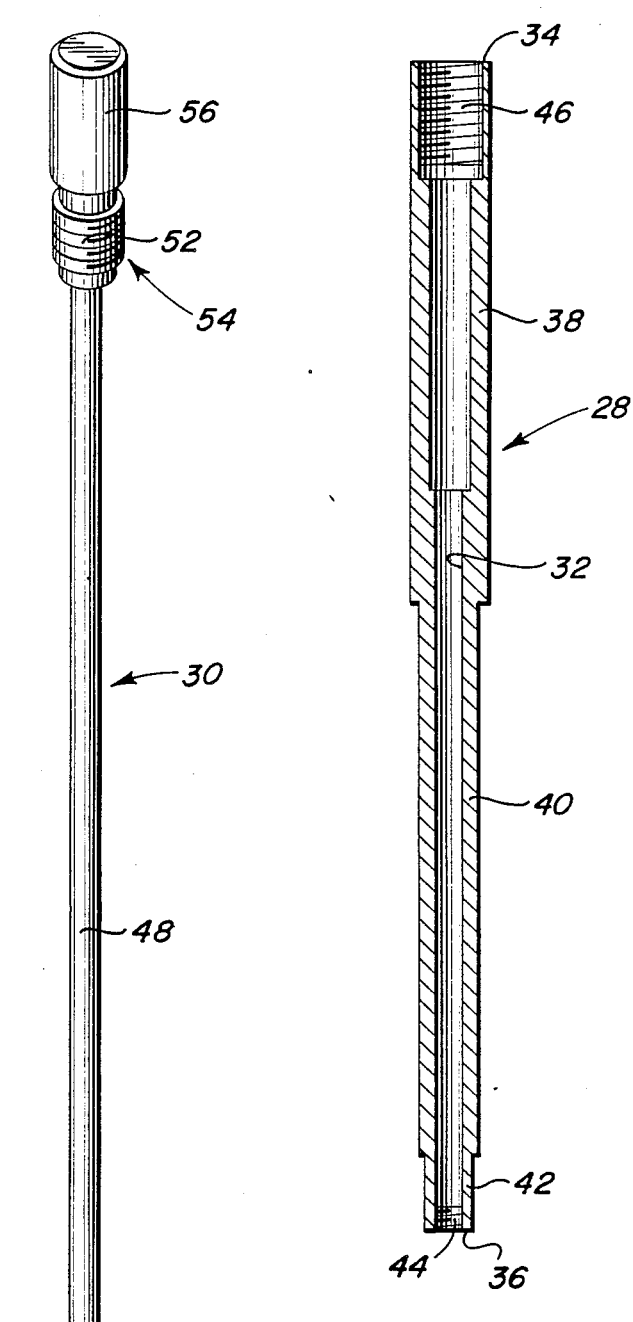
FIG. 1
FIG. 7
FIG. 8
FIG. 2
FIG. 3

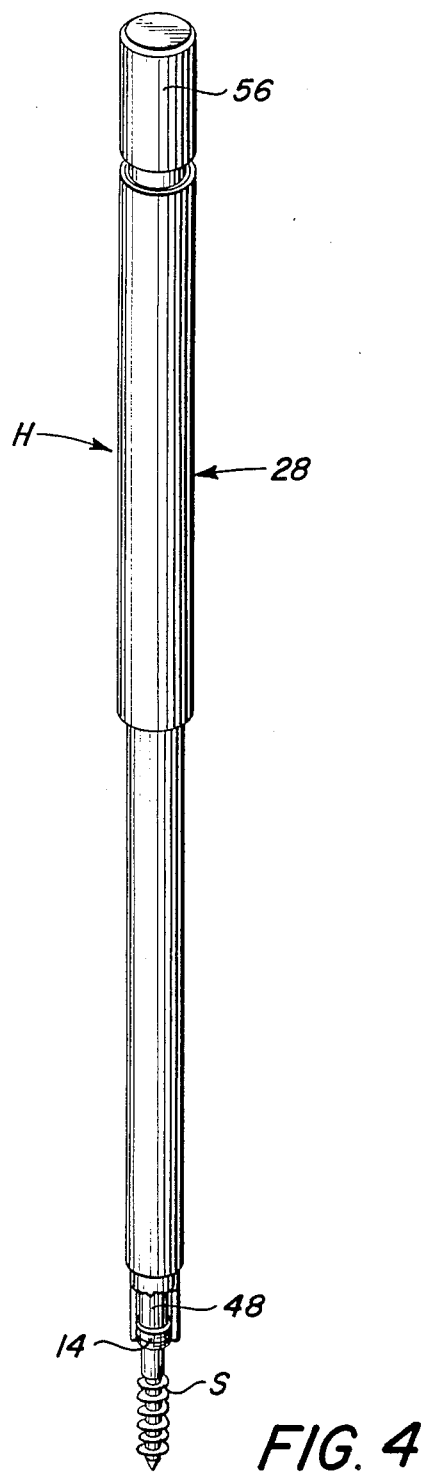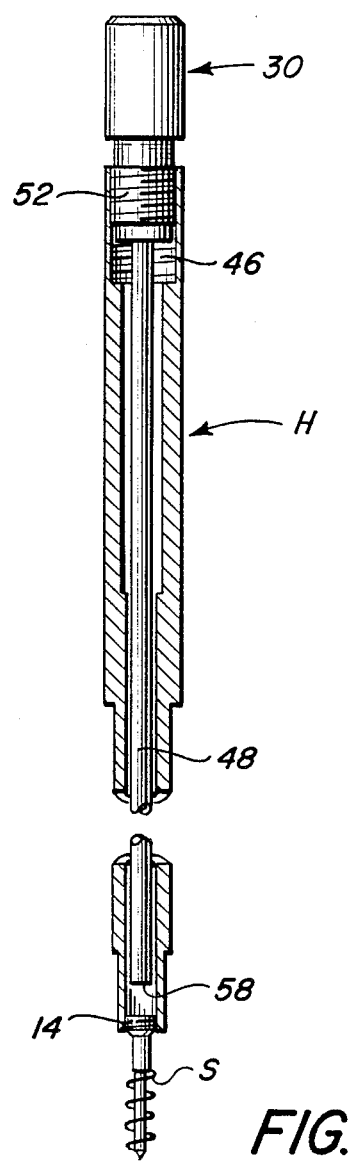
FIG. 4
FIG. 5

BONE SCREW FIXATION ASSEMBLY, BONE SCREW THEREFOR AND METHOD OF FIXATION

BACKGROUND OF THE INVENTION

Osteochondritis dissecans is a condition wherein a small fragment of bone becomes separated from one of the femoral condyles. The usual treatment is debridement and drilling, followed by insertion of a fixation device. Commonly used fixation devices include wires, screws, nails and pins.

The conventional treatment techniques suffer from a number of drawbacks and limitations. For example, wires do not form a secure fixation of the fragment to the femoral condyle and, in addition, a wire may protrude from the fragment. Should the knee be moved while the wire is protruding, then the proximal tibia of the knee joint may be gouged.

Screws have also been used to internally fix the fragment to the femoral condyle, but screws likewise suffer from drawbacks. The typical bone screw has a cruciate head providing an irregular, interrupted surface facing the tibial plateau. As a result, movement of the knee may cause gouging of the tibial plateau as the interrupted area is engaged.

Regardless of the fixation device utilized, it is advantageous that the device be secured in a fixation assembly permitting manipulation of the fragment, and insertion and withdrawal of the fixation device, all with relative ease. There has been a tendency for insertion of the fixation device to be performed anthroscopically, thereby presenting a relatively small portal for the entrance of the fixation device and fixation device holder.

Those skilled in the art will appreciate that there is a need for a bone screw which may be readily installed for securely fixing the bone fragment to the femoral condyle, while also minimizing the possibility of the proximal tibia becoming gouged during movement of the joint. There is likewise a need for a bone screw holder which is easy to manipulate, which securely grasps the bone screw in order to facilitate manipulation of the fragment and insertion of the screw, and which readily seizes the bone screw in order to permit its removal after the treatment is completed. The disclosed invention is just such a bone screw and bone screw holder.

OBJECTS AND SUMMARY OF THE INVENTION

The primary object of the disclosed invention is to provide a bone screw which has a continuously arcuate and uninterrupted head for minimizing gouging of the proximal tibia during movement of the knee joint while the bone screw is inserted into the fragment.

An additional object of the disclosed invention is a bone screw fixation device which utilizes a jam rod for positively securing the bone screw within the screw holder so that movement of the bone screw relative to the holder is avoided.

A bone screw fixation device pursuant to the invention comprises a longitudinally extending member having an aperture therethrough defining an inner wall with spaced first and second end portions. First thread means are formed in the inner wall at the first end portion for receiving cooperating second thread means disposed about the exterior of a fixation device. A longitudinally extending rod means has first and second end portions, and the rod means is receivable in the member aperture for permitting the rod means first end portion to engage the fixation device when the fixation device is received within the member first end portion. Means are operably associated with the member for selectively locking the rod means in engagement with the received fixation device, so that movement of the first thread means relative to the second thread means is prevented.

A fixation device comprises a cylindrical shank having first and second end portions. First thread means are formed in the first end portion and extend toward but terminate short of the second end portion. A head is integral with the second end portion, and the head has a first portion secured to the shank, an oppositely disposed portion having a continuous uninterrupted arcuate surface, and a side rim extending between the portions. Second thread means are formed about the rim.

A bone screw insertion assembly comprises a longitudinally extending member having a central aperture therethrough for defining an inner wall having spaced first and second end portions. First thread means are formed in the inner wall at the first end portion. A bone screw has a head with second thread means formed exteriorly thereabout, and the second thread means are in threaded engagement with the first thread means so that the bone screw is operably associated with and extends from the member. A rod means is received within the aperture and has a first end portion engaged with the bone screw, and applies a force thereto so that movement of the first thread means relative to the second thread means is prevented. Means are operably associated with the member for selectively locking the rod means in engagement with the bone screw.

The method of securing a bone screw to a holder comprises providing a tubular screw holder having a central aperture therethrough defining an inner wall. A first set of threads are formed in the inner wall at a first end portion thereof. A bone screw is provided, and the bone screw has a head and a second set of threads formed about the head. The cooperating first and second sets of threads are threadedly engaged so that the bone screw is attached to the holder and extends therefrom. A rod means is positioned in the aperture so that an end of the rod means engages the bone screw and presses the first and second sets of threads together, thereby preventing movement of the threads relative to each other. The rod means is locked in position, thereby securing the bone screw to the member.

These and other objects and advantages of the invention will be readily apparent in view of the following description and drawings of the above described invention.

DESCRIPTION OF THE DRAWINGS

The above and other objects and advantages and novel features of the present invention will become apparent from the following detailed description of the preferred embodiment of the invention illustrated in the accompanying drawings, wherein:

FIG. 1 is a perspective view of the bone screw of the invention;

FIG. 2 is a perspective view of a jam rod used with the bone screw holder of the invention;

FIG. 3 is a cross-sectional view through the bone screw holder of the invention;

FIG. 4 is a perspective view with portions broken away disclosing the bone screw of FIG. 1 connected to the screw holder and jam rod of FIGS. 2 and 3;

FIG. 5 is a fragmentary elevational view with portions broken away disclosing the jam rod removed from the bone screw;

FIG. 7 is a cross-sectional view of the bone screw of FIG. 1; and,

FIG. 8 is a fragmentary perspective view of the end of the jam rod of FIG. 2.

DETAILED DESCRIPTION OF THE INVENTION

Figure 6:
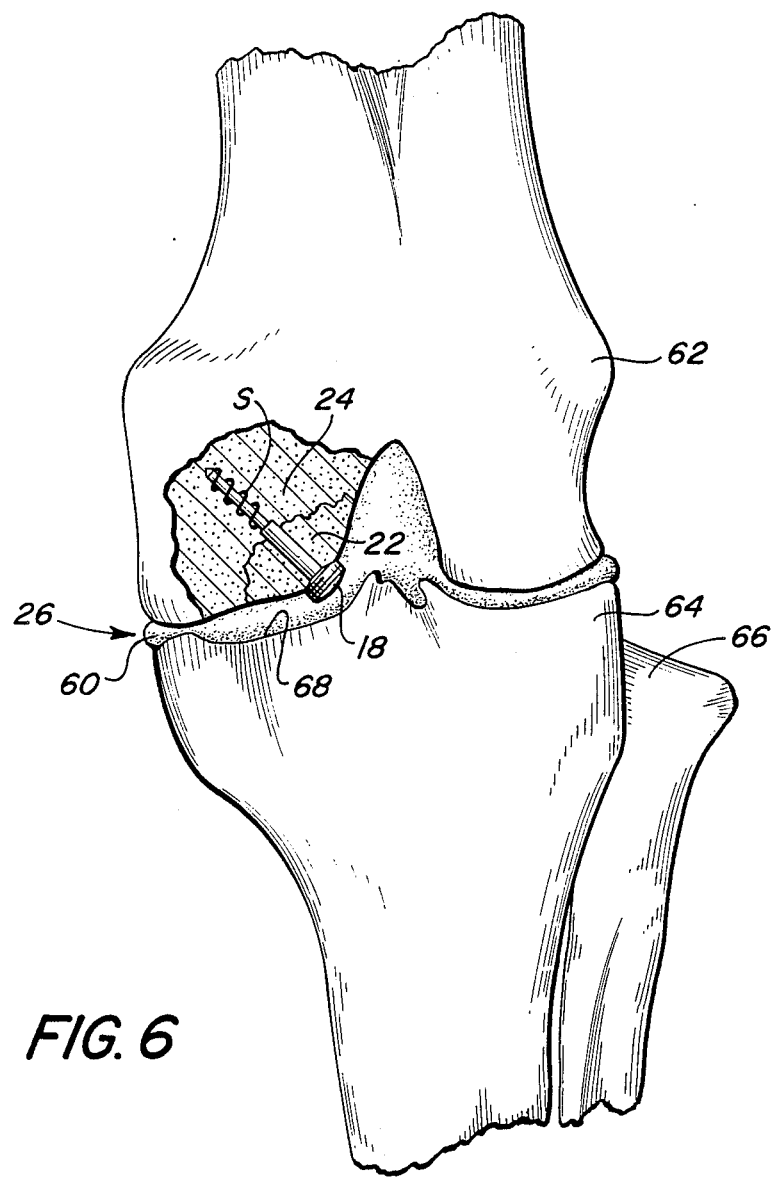
FIG. 6 is an elevational view disclosing the bone screw of FIG. 1 inserted into a knee joint.

Bone screw S, as best shown in FIGS. 1 and 7, has a central cylindrical shank 10 from which threads 12 and head 14 extend from opposite ends thereof. The head 14 is integral with shank 10 and has a lower arcuately upwardly extending surface 16 extending from the shank 10, and an upper arcuate uninterrupted surface 18 oppositely disposed relative thereto. The arc of the surface 18 is centered on a point disposed in the direction of threads 12, as best shown in FIG. 7. A rim portion extends peripherally about head 14 between the surfaces 16 and 18, and threads 20 are formed about the rim portion. I have found that two threads 20 are sufficient for secure fixation of the bone screw S. Those skilled in the art will understand that the bone screw S is a lag screw. A lag screw is useful for causing a detached bone fragment, such as the fragment 22 of FIG. 6, to be drawn to the femoral condyle 24 of knee joint 26.

Screw holder H, as best shown in FIGS. 4 and 5, comprises a tubular member 28 in which jam rod 30 is movably received. The screw holder H and bone screw S are, preferably, formed of a surgical grade of stainless steel.

Tubular member 28, as best shown in FIG. 3, has a central longitudinally extending aperture 32 extending between the spaced ends 34 and 36 thereof. It can be noted in FIG. 3 that the tubular member 28 has an enlarged diameter portion 38 proximate end 34, a portion 40 of intermediate diameter, and a reduced diameter portion 42 proximate second end 36. The portion 38 has the largest diameter in order to facilitate the holder H being grasped and manipulated by the surgeon, while the portion 42 has the smallest diameter in order to minimize the size of the incision which must be made for insertion or removal of the bone screw S.

FIG. 3 also discloses first threads 44 formed in the inner wall of third portion 42 at end 36. The threads 44 cooperate with the threads 20 of screw S so that the head 14 may be screwed into the third tubular portion 42. Second threads 46 are formed in first tubular portion 38 at end 34 for reasons to be explained. The threads 44 and 46 are commonly rotatable either clockwise or counterclockwise.

Jam rod 30, as best shown in FIG. 2, has a central shaft 40 which is receivable within aperture 32 of tubular member 28. Shaft 48, as best shown in FIG. 8, has a central inwardly directed arcuate recess 50 which conforms to the curvature of surface 18 of screw S.

Third threads 52 are formed about enlarged diameter portion 54 Of jam rod 30, as best shown in FIG. 2. The threads 52 cooperate with the threads 46 of tubular member 28, so that the shaft 48 may be advanced or retracted relative to end 36 by appropriate rotation of jam rod 30. FIG. 2 also discloses handle element 56 extending longitudinally beyond enlarged diameter portion 54. The handle portion 56, as best shown in FIG. 4, extends beyond tubular member 28 in order to facilitate rotation of jam rod 30 while shaft 48 is being advanced toward or disengaged from a screw S. The handle element 56 and enlarged diameter portion 54 are larger in diameter than the shaft 48 and threads 46 in order to provide a mechanical advantage as the bone screw S is being engaged by the recess 50. The larger diameter requires less force to be applied by the surgeon as the bone screw S is being grasped. This maximizes the clamping force applied to the threads 44 and 20, thereby preventing rotation of one relative to the other.

FIG. 5 discloses screw holder H with a screw S threaded into third tubular portion 42, but with the recess 50 removed from head 14. As a result, the screw S is free to rotate relative to the first threads 44, at least to the extent of the length of the first threads 44. Because the recess 50 of the end 58 is not engaged with the surface 18 of head 14, there is no positive securement of the screw S relative to the holder H. This situation would typically be utilized when the screw S was being prepared for removal from the bone, or when it was being attached to the holder H for insertion.

FIG. 4 discloses the holder H with the end 58 of the jam rod 30 in engagement with the head 14. Because the jam rod 30 extends between the ends 34 and 36, it exerts sufficient force on the head 14 to lock the threads 20 and 44 together, thereby preventing rotation of the bone screw S relative to the tubular member 28. The force applied to the screw S by the jam rod 30 is also sufficient to prevent further rotation of the jam rod 30. As a result, the threads 52 and 46 become locked together, and assure that a constant locking force is applied to the head 14 by the end 58 of shaft 48.

The locking force applied to the screw S by the jam rod 30 is sufficient to prevent rotation of the bone screw S relative to the holder H in either the clockwise or counterclockwise direction. As a result, the screw S may be threaded into bone portion 24 for affixing the bone fragment 22 thereto. Alternatively, when removal of the screw S is desired, the holder H may once again be locked to the screw S, and the screw removed. In either event, fixation of the bone screw S to the holder H is accomplished relatively easily, and yet provides positive securement.

FIG. 6 discloses the screw S inserted into knee joint 26 for fixing the fragment 22 relative to one femoral condyle 24. Those skilled in the art appreciate that articular cartilage 60 is disposed between the cooperating ends of the bones 62, 64 and 66 of knee joint 26. The head 14 has the uninterrupted continuous surface 18 facing the tibial plateau 68, but, because it is an uninterrupted surface, it minimizes gouging of the tibial plateau 68 during movement of the joint 26.

The bone screw S provides a smooth uninterrupted surface 18 which minimizes gouging of the tibial plateau 68 and, because of its arcuate contour, permits the tibial plateau 68 to glide therealong. The threads 20 of the head 14 are buried in the articular cartilage 60 so that they do not engage the tibial plateau 68. The cartilage 60 is relatively soft, thereby permitting the screw S to be inserted until the surface 16 engages the bone fragment 22. The articular cartilage 60 is basically forced out of the way by the advancing bone screw S. As a result, only the arcuate uninterrupted surface 18 is presented for possible contact with the tibial plateau 68.

The screw S and the screw holder H form an integral device, with the screw S being held against rotation relative to the holder H. As a result, manipulation of the fragment 22 can be carried out by using the screw holder H and screw S as a single unit. In other words, the integral screw holder H and screw S may be used to manipulate the fragment 22 into position relative to the femoral condyle 24, and the screw then inserted therein in order to fixate the fragment 22 thereto.

The unique configuration of the screw S also permits its removal, upon completion of treatment, without requiring that the underlying cartilage 60 be disturbed. Additionally, when the screw S is anthroscopically inserted, the portal of the entrance of the holder H exactly anatomically aligns with the screw S itself, thereby facilitating removal at a later date through like anthroscopic means.

While this invention has been described as having a preferred design, it is understood that it is capable of further modifications, uses and/or adaptations of the invention, following in general the principle of the invention, and including such departures from the present disclosure as come within known or customary practice in the art to which the invention pertains, and as may be applied to the central features hereinbefore set forth, and fall within the scope of the invention of the limits of the appended claims.

What is claimed is:

1. A bone screw fixation assembly, comprising:
   (a) a longitudinally extending member having an aperture therethrough defining an inner wall with spaced first and second end portions;
   (b) first thread means formed in said inner wall at said first end portion for receiving cooperating second thread means disposed about the exterior of a headed fixation device having an uninterrupted and arcuate terminal end;
   (c) longitudinally extending rod means having a first arcuate end portion and a second spaced end portion, said rod means receivable in said aperture for permitting said rod means first end portion to engage the fixation device when received within said member first end portion and said first arcuate end portion extends in substantially the same direction as the terminal end of the fixation device; and,
   (d) means operably associated with said member for selectively locking said rod means in engagement with the received fixation device so that the movement of said first thread means relative to the second thread means is prevented.

2. The assembly of claim 1, wherein:
   (a) said rod means has a length at least equal to the distance between said member first and second end portions so that said rod means extends therebetween when received in said member.

3. The assembly of claim 1, wherein:
   (a) said locking means are operably associated with said member second end portion.

4. The assembly of claim 3, wherein said locking means includes:
   (a) third thread means formed in said inner wall at said member second end portion; and,
   (b) fourth thread means formed about said rod means second end portion and cooperating with said third thread means so that engagement of said rod means first end portion with the fixation device prevents said third and fourth thread means from moving relative to each other.

5. The assembly of claim 4, wherein:
   (a) said first and third thread means are commonly rotatable.

6. The assembly of claim 4, wherein:
   (a) said member first end portion has an external diameter less than the external diameter of said member second end portion.

7. The assembly of claim 2, wherein:
   (a) said rod means second end portion includes a handle element disposed exteriorly of said member second end portion.

8. The assembly of claim 4, wherein:
   (a) said rod means second end portion includes a handle element disposed exteriorly of said member second end portion, and said third thread means are disposed intermediate said handle element and said rod means first end portion.

9. The assembly of claim 1, wherein:
   (a) said rod means first end portion includes an arcuate recess conforming to the fixation element.

10. A fixation device, comprising:
    (a) a cylindrical shank having first and second end portions;
    (b) first thread means formed in said first end portion extending toward but terminating short of said second end portion;
    (c) a head mounted to said second end portion, said head having an upper surface being uninterrupted and arcuate, and a side rim extending from said upper surface; and,
    (d) second thread means formed about said side rim.

11. The device of claim 10, wherein:
    (a) said rim has a diameter exceeding the diameter of said shank.

12. The device of claim 10, wherein:
    (a) said head includes a lower surface secured to said shank, said lower surface extends arcuately from said shank toward said rim.

13. The device of claim 10, wherein
    (a) said second thread means has no more than two threads.

14. A bone screw insertion assembly, comprising:
    (a) a longitudinally extending member having a central aperture therethrough defining an inner wall with spaced first and second end portions;
    (b) first thread means formed in said inner wall at said first end portion;
    (c) a bone screw having a head with second thread means formed exteriorly thereabout and an upper surface being arcuate and uninterrupted, said second thread means in threaded engagement with said first thread means so that said bone screw is operably associated with said member and extends therefrom;
    (d) rod means received within said aperture and having a first end portion engaged with and conforming to said bone screw upper surface for applying a force thereto so that movement of said first thread means relative to said second thread means is prevented; and,
    (e) means operably associated with said member for selectively locking said rod means in engagement with said bone screw.

15. The assembly of claim 14, wherein said locking means includes:
    (a) third thread means formed in said inner wall at said second end portion; and, (b) fourth thread means cooperating with said third thread means formed about said rod means at a second end portion thereof so that engagement of said rod means first end portion with said bone screw causes said third and fourth thread means to be locked together for thereby locking said rod means thereto.

16. The assembly of claim 15, wherein:
(a) said rod means second end portion includes a handle element, and said fourth thread means are disposed intermediate said handle element and said rod means first end portion.

17. The method of securing a bone screw, comprising:
(a) providing a tubular screw holder having a central aperture therethrough defining an inner wall with a first set of threads formed therein at a first end portion thereof;
(b) providing a bone screw having a head which has an upper surface being arcuate and uninterrupted and a second set of threads formed about the head;
(c) threadedly engaging the first and second sets of threads so that the bone screw is attached to the holder and extends therefrom;
(d) positioning a rod means in the aperture so that an end of the rod means engages the bone screw upper surface and presses the first and second sets of threads together so that movement of the sets of threads relative to each other is prevented; and,
(e) locking the rod means.

18. The device of claim 10, wherein:
(a) said uninterrupted surface is continuous.

19. The device of claim 10, wherein:
(a) said second thread means includes no more than 20. A method as in claim 17, comprising the further step of:
(a) providing the bone screw with a substantially convex head; and
(b) providing a concavity, operably associated with the convex head, in the end of the rod means that engages the bone screw.

21. A method as in claim 17, further including the step of:
(a) inserting the bone screw into a bone such that the second set of threads formed about the head of the bone screw protrude from the bone; and
(b) disengaging the bone screw from the tubular screw holder.

22. A method as in claim 21, further including the step of:
(a) engaging the first and second set of threads at a position removed from the bone so as to prevent movement of the set of threads relative to each other; and
(b) withdrawing the bone screw from the bone.

* * * * *